US011946062B2

(12) United States Patent
Zhang et al.

(10) Patent No.: US 11,946,062 B2
(45) Date of Patent: Apr. 2, 2024

(54) GENE PpHSP21 WITH BLACK SPOT DISEASE RESISTANCE IN PYRUS PYRIFOLIA AND ITS APPLICATIONS IN IMPROVING BLACK SPOT DISEASE RESISTANCE IN PLANTS

(71) Applicant: Nanjing Agricultural University, Jiangsu (CN)

(72) Inventors: Shaoling Zhang, Jiangsu (CN); Xiaosan Huang, Jiangsu (CN); Caihua Xing, Jiangsu (CN); Qinghai Qiao, Jiangsu (CN); Zhihua Xie, Jiangsu (CN); Likun Lin, Jiangsu (CN); Kaijie Qi, Jiangsu (CN); Huizhen Dong, Jiangsu (CN)

(73) Assignee: NANJING AGRICULTURAL UNIVERSITY, Jiangsu (CN)

( * ) Notice: Subject to any disclaimer, the term of this patent is extended or adjusted under 35 U.S.C. 154(b) by 0 days.

(21) Appl. No.: 17/390,776

(22) Filed: Jul. 30, 2021

(65) Prior Publication Data
US 2021/0371874 A1     Dec. 2, 2021

(30) Foreign Application Priority Data

Jul. 30, 2020    (CN) .......................... 202010750114.3

(51) Int. Cl.
    C12N 15/82      (2006.01)
    C07K 14/415     (2006.01)
(52) U.S. Cl.
    CPC ..... *C12N 15/8282* (2013.01); *C12N 15/8205* (2013.01); *C07K 14/415* (2013.01)
(58) Field of Classification Search
    None
    See application file for complete search history.

(56) References Cited

U.S. PATENT DOCUMENTS

2003/0162294 A1* 8/2003 Verbruggen ....... C12N 15/8216
                                                            536/25.4

FOREIGN PATENT DOCUMENTS

CN      110724692    *  1/2020
WO    WO-2012151071 A2 * 11/2012 .......... C12N 15/8216

OTHER PUBLICATIONS

Zurn et al. "Mapping a Novel Black Spot Resistance Locus in the Climbing Rose Brite EyesTM ('RADbrite')" 2018 Front. Plant Sci. 9:1730 doi: 10.3389/fpls.2018.01730 (7 total pages) (Year: 2018).*

(Continued)

*Primary Examiner* — Matthew R Keogh
*Assistant Examiner* — Rebecca Stephens
(74) *Attorney, Agent, or Firm* — Tutunjian & Bitetto, P.C.

(57) ABSTRACT

A gene PpHSP21 with black spot disease resistance is isolated from *Pyrus pyrifolia*. A nucleotide sequence of the gene PpHSP21 is shown in SEQ ID NO. 1. An amino acid sequence of an encoded protein of the PpHSP21 gene is shown in SEQ ID NO. 2. By constructing the plant overexpression vector and silencing vector of the gene PpHSP21, the gene PpHSP21 is introduced into the plant by the *Agrobacterium*-mediated genetic transformation method, so that the gene PpHSP21 is able to be overexpressed in the plants, thereby significantly improving black spot disease resistance in plants. The discovery and identification of the gene PpHSP21 provide new genetic resources for stress resistance molecular design and breeding in plants, and to provide new genetic resources for the implementation of green agriculture. The development and utilization of the genetic resources is conducive to reducing agricultural production costs and achieving environmental friendliness.

1 Claim, 9 Drawing Sheets

Specification includes a Sequence Listing.

(56) References Cited

OTHER PUBLICATIONS

Yang et al. "Candidate Resistant Genes of Sand Pear (*Pyrus pyrifolia Nakai*) to Alternaria alternata Revealed by Transcriptome Sequencing" 2015 PLoS One 10(8): e0135046 (pp. 1-17). (Year: 2015).*

UniProtKB Accession No. A0A5N5F165_9ROSA (version 3, published Jun. 17, 2020) (Year: 2020).*

Yang et al. "Screening of Pyrus pyrifolia genotypes for resistance to Alternaria alternata" 2020 Scientia Horticulturae 259: 108838 (8 total pages), published online Sep. 12, 2019) (Year: 2019).*

* cited by examiner 6-4　　HS960　　7-2

The leaves of 587 varieties were inoculated with different black spot disease strains after 4 days

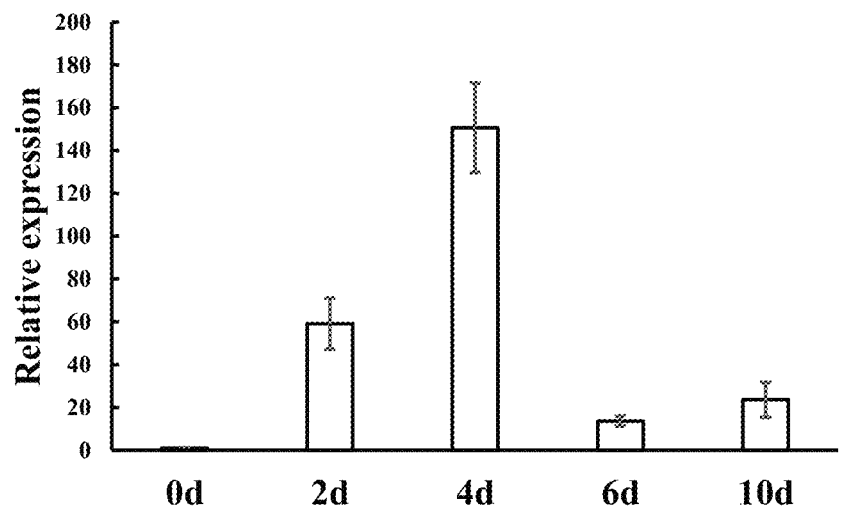
Fig. 6B
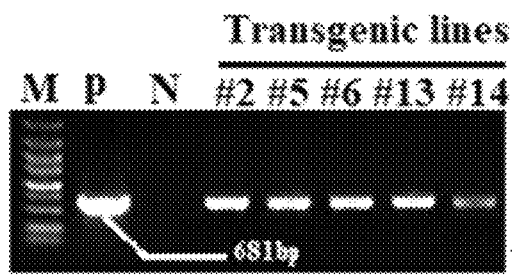
Fig. 7A
Fig. 7B                     Fig. 7C
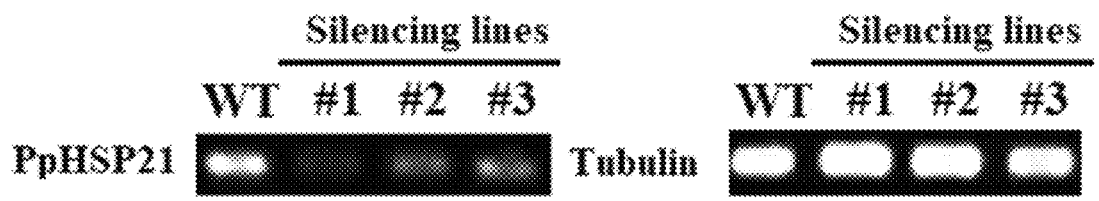
Fig. 7D                     Fig. 7E

SEQUENCE LISTING

<160> NUMBER OF SEQ ID NOS: 14

<210> SEQ ID NO 1
<211> LENGTH: 681
<212> TYPE: DNA
<213> ORGANISM: Artificial Sequence
<220> FEATURE:
<223> OTHER INFORMATION: Synthesis

<400> SEQUENCE: 1

```
atggcttcaa cattggcttt gtcttcttcg tcacctttgc tttcaaacaa agcaaggtct      60
tcaatcacag caaacgccac tctgccatcc tcggccgcct ttccgttgcg gcggaatagg     120
ctgccggtgg tgagagctca ggccggtgga gacggcaagt tggacgtgca agtcaatcag     180
ggcaaccaag ggactgatgt ggagaggagg ccaaagagat tggctgtgga catttctcct     240
tttggtattg caggtctatt agatcccatc tccccagtga gaacaatgcg gcaaatgctg     300
gacacagtcg accggctttt cgaagacacg gtggcattcc cgggaagaaa cagagcagca     360
ggggaagtgc gcgcgccttg ggacatcaaa gacgacgaac acgaaatcaa aatgcggttc     420
gacatgccgg ggctttcgaa ggaggacgtg aaggtgtcgg tcgaggacga tgtgctagtt     480 ataaaggggag agcagaagaa ggaagaaggc ggcgacgatt cgtggtcgag caggagcttt     540
agctcctaca atacccgcct tcagctaccg gataattcgg agaaggacaa gatcaaggcg     600
gagttcaaga atggtgttct ctacatagcc attcctaaga ccaaagttga acgcaaggtt     660
attgacgttg caattcagtg a                                               681
```

<210> SEQ ID NO 2
<211> LENGTH: 226
<212> TYPE: PRT
<213> ORGANISM: Artificial Sequence
<220> FEATURE:
<223> OTHER INFORMATION: Synthesis

<400> SEQUENCE: 2

```
Met Ala Ser Thr Leu Ala Leu Ser Ser Ser Ser Pro Leu Leu Ser Asn
1               5                   10                  15

Lys Ala Arg Ser Ser Ile Thr Ala Asn Ala Thr Leu Pro Ser Ser Ala
            20                  25                  30
```

Ala Phe Pro Leu Arg Arg Asn Arg Leu Pro Val Val Arg Ala Gln Ala
            35                  40                  45

Gly Gly Asp Gly Lys Leu Asp Val Gln Val Asn Gln Gly Asn Gln Gly
 50                  55                  60

Thr Asp Val Glu Arg Arg Pro Lys Arg Leu Ala Val Asp Ile Ser Pro
 65                  70                  75                  80

Phe Gly Ile Ala Gly Leu Leu Asp Pro Ile Ser Pro Val Arg Thr Met
                 85                  90                  95

Arg Gln Met Leu Asp Thr Val Asp Arg Leu Phe Glu Asp Thr Val Ala
            100                 105                 110

Phe Pro Gly Arg Asn Arg Ala Ala Gly Glu Val Arg Ala Pro Trp Asp
            115                 120                 125

Ile Lys Asp Asp Glu His Glu Ile Lys Met Arg Phe Asp Met Pro Gly
130                 135                 140

Leu Ser Lys Glu Asp Val Lys Val Ser Val Glu Asp Asp Val Leu Val
145                 150                 155                 160

Ile Lys Gly Glu Gln Lys Lys Glu Gly Gly Asp Asp Ser Trp Ser
                165                 170                 175

Ser Arg Ser Phe Ser Ser Tyr Asn Thr Arg Leu Gln Leu Pro Asp Asn
            180                 185                 190

Ser Glu Lys Asp Lys Ile Lys Ala Glu Phe Lys Asn Gly Val Leu Tyr
            195                 200                 205

Ile Ala Ile Pro Lys Thr Lys Val Glu Arg Lys Val Ile Asp Val Ala
            210                 215                 220

Ile Gln
225

<210> SEQ ID NO 3
<211> LENGTH: 23
<212> TYPE: DNA
<213> ORGANISM: Artificial Sequence
<220> FEATURE:
<223> OTHER INFORMATION: Synthesis

<400> SEQUENCE: 3
atggcttcaa cattggcttt gtc                                              23

<210> SEQ ID NO 4
<211> LENGTH: 22
<212> TYPE: DNA
<213> ORGANISM: Artificial Sequence
<220> FEATURE:
<223> OTHER INFORMATION: Synthesis

<400> SEQUENCE: 4
ctgaattgca acgtcaataa cc                                               22

<210> SEQ ID NO 5
<211> LENGTH: 44
<212> TYPE: DNA
<213> ORGANISM: Artificial Sequence
<220> FEATURE:
<223> OTHER INFORMATION: Synthesis

<400> SEQUENCE: 5
gagaacacgg gggactctag aatggcttca acattggctt tgtc                       44

<210> SEQ ID NO 6
<211> LENGTH: 43
<212> TYPE: DNA

```
<213> ORGANISM: Artificial Sequence
<220> FEATURE:
<223> OTHER INFORMATION: Synthesis

<400> SEQUENCE: 6
gcccttgctc accatggatc cctgaattgc aacgtcaata acc              43

<210> SEQ ID NO 7
<211> LENGTH: 42
<212> TYPE: DNA
<213> ORGANISM: Artificial Sequence
<220> FEATURE:
<223> OTHER INFORMATION: Synthesis

<400> SEQUENCE: 7
aaggttaccg aattctctag agacatcaaa gacgacgaac ac               42

<210> SEQ ID NO 8
<211> LENGTH: 43
<212> TYPE: DNA
<213> ORGANISM: Artificial Sequence
<220> FEATURE:
<223> OTHER INFORMATION: Synthesis

<400> SEQUENCE: 8
tgtcttcggg acatgcccgg gctgaattgc aacgtcaata acc              43

<210> SEQ ID NO 9
<211> LENGTH: 22
<212> TYPE: DNA
<213> ORGANISM: Artificial Sequence
<220> FEATURE:
<223> OTHER INFORMATION: Synthesis

<400> SEQUENCE: 9
ggtgtcatgg ttggtatggg tc                                     22

<210> SEQ ID NO 10
<211> LENGTH: 23
<212> TYPE: DNA
<213> ORGANISM: Artificial Sequence
<220> FEATURE:
<223> OTHER INFORMATION: Synthesis

<400> SEQUENCE: 10
cctctgtgag tagaactggg tgc                                    23

<210> SEQ ID NO 11
<211> LENGTH: 23
<212> TYPE: DNA
<213> ORGANISM: Artificial Sequence
<220> FEATURE:
<223> OTHER INFORMATION: Synthesis

<400> SEQUENCE: 11
tctccttttg gtattgcagg tct                                    23

<210> SEQ ID NO 12
<211> LENGTH: 20
<212> TYPE: DNA
<213> ORGANISM: Artificial Sequence
<220> FEATURE:
<223> OTHER INFORMATION: Synthesis

<400> SEQUENCE: 12
ggcatgtcga accgcatttt                                        20
```

-continued

```
<210> SEQ ID NO 13
<211> LENGTH: 19
<212> TYPE: DNA
<213> ORGANISM: Artificial Sequence
<220> FEATURE:
<223> OTHER INFORMATION: Synthesis

<400> SEQUENCE: 13
tgggctttgc tcctcttac                                                 19

<210> SEQ ID NO 14
<211> LENGTH: 19
<212> TYPE: DNA
<213> ORGANISM: Artificial Sequence
<220> FEATURE:
<223> OTHER INFORMATION: Synthesis

<400> SEQUENCE: 14
ccttcgtgct catcttacc                                                 19
```

GENE PpHSP21 WITH BLACK SPOT DISEASE RESISTANCE IN PYRUS PYRIFOLIA AND ITS APPLICATIONS IN IMPROVING BLACK SPOT DISEASE RESISTANCE IN PLANTS

CROSS REFERENCE OF RELATED APPLICATION

The present invention claims priority under 35 U.S.C. 119(a-d) to CN 202010750114.3, filed Jul. 30, 2020.

INCORPORATION-BY-REFERENCE OF THE SEQUENCE LISTING

The Sequence Listing associated with this application is provided in text file, and is hereby incorporated by reference into the specification. The name of the text file containing the Sequence Listing is BJP773Sequencelisting.txt. The text file is 6 KB, was created on Aug. 5, 2021, and is being submitted electronically via EFS-Web.

BACKGROUND OF THE PRESENT INVENTION

Field of Invention

The present invention relates to the field of genetic engineering technology, and more particularly to a gene PpHSP21 with black spot disease resistance which is isolated from *Pyrus pyrifolia* and applications of gene PpHSP21.

Description of Related Arts

*Pyrus* spp. (pear) is one of the most productive fruits in the world and originate in the mountainous areas of western and southwestern China. With the global warming, the frequent occurrence of extreme climate events has led to more and more biological and abiotic stresses on *Pyrus* spp. Black spot disease is one of the main biological stresses that affect the growth, development, yield and fruit quality of *Pyrus* spp. If the disease occurs on leaves, black spots as rice grains appear on the leaves in the early stage, and then are continuously increasing in area to be circular or nearly circular, and are getting darker in color from gray black to dark brown. If the disease occurs in fruits, round or oval spots appear on the surface of fruits, usually black or dark brown, and moreover, the surface of fruits is slightly sunken, and the diseased fruits rot seriously and fall easily. If the disease occurs on branches, elliptical or irregular obvious depressions are formed in the surface of branches, cracks will often appear at junctions of disease and health, and tips of branches are easy to be broken or died. Therefore, the black spot disease seriously affects the yield and quality of *Pyrus* spp.

*Pyrus pyrifolia* is a widely cultivated cultivar with strong resistance to black spot disease. It is an ideal material for studying the disease resistance of woody plants and cloning related disease resistance genes. Therefore, it is the key and basis for disease resistance genetic engineering to clone genes in *Pyrus pyrifolia* which are related to disease resistance.

SUMMARY OF THE PRESENT INVENTION

In view of this, an object of the present invention is to provide a gene PpHSP21 with black spot disease resistance which is isolated from *Pyrus pyrifolia* and applications of gene PpHSP21, so as to provide new genetic resources for stress resistance molecular design and breeding in plants, and to provide new genetic resources for the implementation of green agriculture. The development and utilization of the genetic resources is conducive to reducing agricultural production costs and achieving environmental friendliness.

Accordingly, to achieve the above object, the present invention provides technical solutions as follows.

A gene PpHSP21 with black spot disease resistance which is isolated from *Pyrus pyrifolia*, wherein a nucleotide sequence of the gene PpHSP21 is shown in SEQ ID NO. 1.

Preferably, the present invention provides an encoded protein of the PpHSP21 gene, an amino acid sequence of the encoded protein is shown in SEQ ID NO. 2.

Preferably, the encoded protein contains 226 amino acids, has an isoelectric point of 9.4 and a molecular weight of 24.92 KDa.

The present invention provides a primer pair for amplifying the gene PpHSP21, the primer pair comprises an upstream pair and a downstream pair, a nucleotide sequence of the upstream pair is shown in SEQ ID NO. 3, a nucleotide sequence of the downstream pair is shown in SEQ ID NO. 4.

Also, the present invention provides an overexpression vector for expressing the gene PpHSP21, wherein the overexpression vector takes pCAMIBA1300 as a basic carrier, and inserts the gene PpHSP21 between Xbal I and BamH I restriction sites of the basic vector.

Also, the present invention provides applications of the gene PpHSP21 or the overexpression vector in genetic improvement of black spot disease resistance in plants.

Preferably, the plants are *Pyrus* spp. or *Arabidopsis thaliana*.

The present invention also provides a method of improving black spot disease resistance in plants, which comprises a step of performing overexpression on the gene PpHSP21 in a genome of the plants, wherein a nucleotide sequence of the gene PpHSP21 is shown in SEQ ID NO. 1.

The present invention provides the gene PpHSP21 with black spot disease resistance which is isolated from *Pyrus pyrifolia*, and an encoded protein of the PpHSP21 gene, wherein a nucleotide sequence of the gene PpHSP21 is shown in SEQ ID NO. 1, an amino acid sequence of the encoded protein is shown in SEQ ID NO. 2. The temporal expression pattern of the gene PpHSP21 in plants under black spot pathogen treatment was analyzed with the qRT-PCR technique, and results showed that the gene PpHSP21 was induced by black spot disease, and the expression level of the gene PpHSP21 is also gradually increased with the treatment time prolonged, the 3d expression level reaches the peak, and then slowly decreases, indicating that the gene PpHSP21 has a very strong response to the black spot stress, and PpHSP21 is a potential gene with black spot disease resistance. By constructing the plant overexpression vector of the gene PpHSP21, the gene PpHSP21 is introduced into the plant by the *Agrobacterium*-mediated genetic transformation method, so that the gene PpHSP21 is able to be overexpressed in the plants (FIG. 1 shows a flow chart), thereby significantly improving the black spot disease resistance in plants. The discovery and identification of the gene PpHSP21 provide new genetic resources for stress resistance molecular design and breeding in plants, and to provide new genetic resources for the implementation of green agriculture. The development and utilization of the genetic resources is conducive to reducing agricultural production costs and achieving environmental friendliness.

BRIEF DESCRIPTION OF THE DRAWINGS

FIG. 6B shows the relative expression of PpHSP21 after the leaves of 'Dangshansuli' pears are inoculated with black spot disease.

FIG. 7A shows the DNA identification of transgenic *Arabidopsis thaliana*.

FIG. 7B shows the overexpression identification of transgenic *Arabidopsis thaliana*.

FIG. 7C shows the semi-quantitative analysis of internal reference genes in wild-type and transgenic *Arabidopsis thaliana*.

FIG. 7D shows the semi-quantitative analysis of PpHSP21 in wild-type and gene-silenced *Pyrus betulaefolia* lines.

FIG. 7E shows the semi-quantitative analysis of internal reference genes in wild-type and gene-silenced *Pyrus betulaefolia* lines.

DETAILED DESCRIPTION OF THE PREFERRED EMBODIMENT

Figure 1:
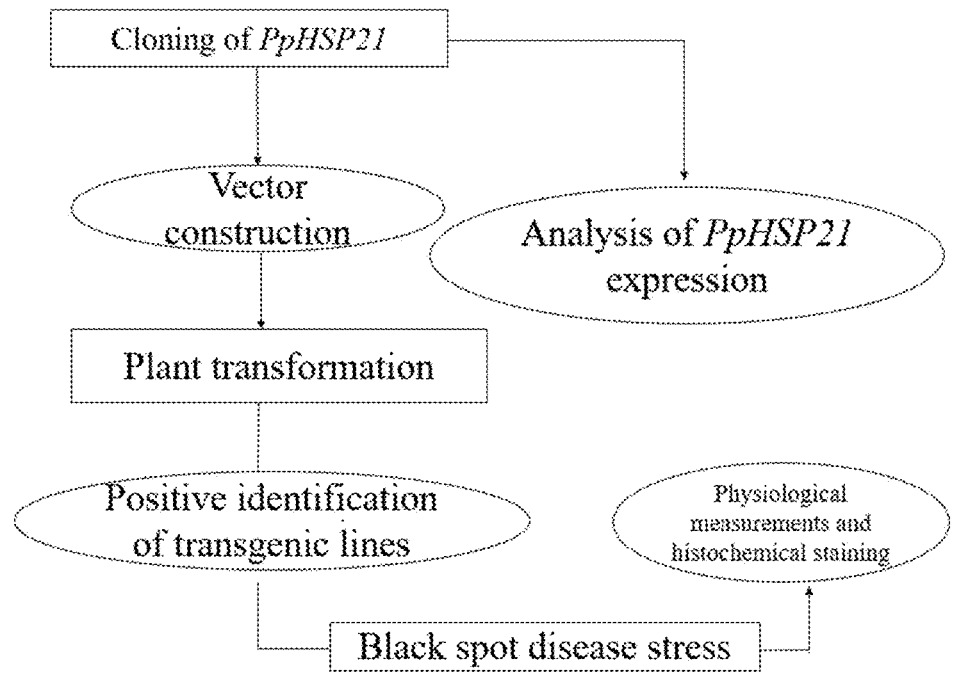
FIG. 1 is a flow chart provided by the present invention.
Figure 2:
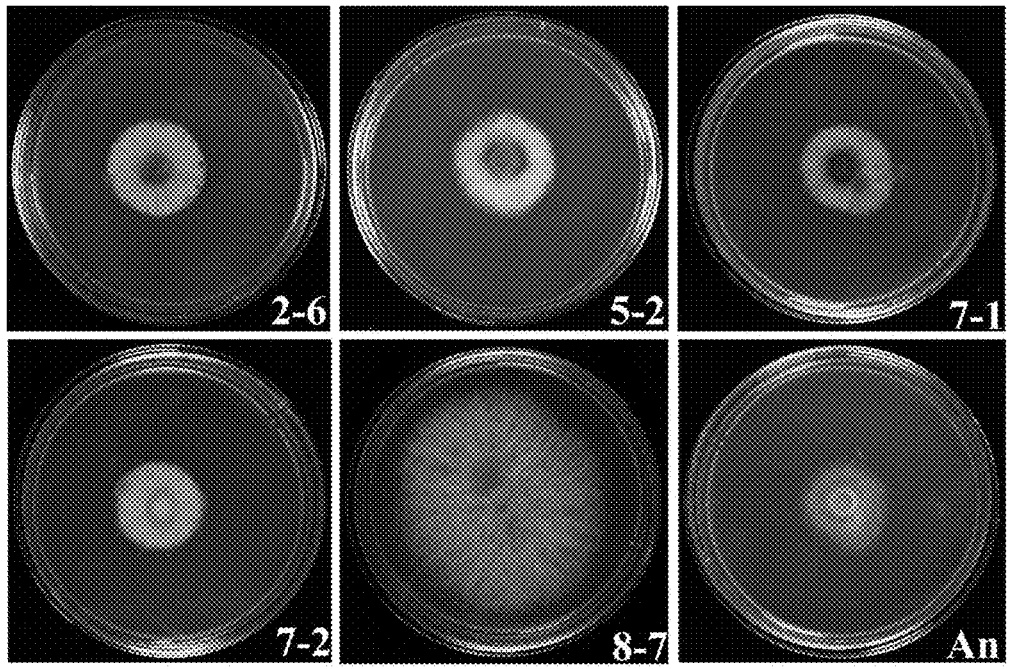
FIG. 2 shows the colony morphology of different black spot disease strains of *Pyrus* spp.

The present invention provides a gene PpHSP21 with black spot disease resistance which is isolated from *Pyrus pyrifolia*, wherein a nucleotide sequence of the gene PpHSP21 is shown in SEQ ID NO. 1. The gene PpHSP21 is a heat shock protein coding genes strongly responsive to black spot disease The present invention provides an encoded protein of the PpHSP21 gene, an amino acid sequence of the encoded protein is shown in SEQ ID NO. 2. The encoded protein preferably contains 226 amino acids, has an isoelectric point of 9.4 and a molecular weight of 24.92 KDa.

The present invention provides a primer pair for amplifying the gene PpHSP21, the primer pair comprises an upstream pair and a downstream pair, a nucleotide sequence of the upstream pair is shown in PpHSP21-F1 (SEQ ID NO. 3): ATGGCTTCAACATTGGCTTTGTC, a nucleotide sequence of the downstream pair is shown in PpHSP21-R1 (SEQ ID NO. 4): CTGAATTGCAACGTCAATAACC.

When the above primer pair is used in the present invention to clone PpHSP21, cDNA of *Pyrus pyrifolia* is preferably taken as a template, a full-length cDNA sequence of the gene PpHSP21 is obtained by cloning with PCR (Polymerase Chain Reaction) technology, wherein the PCR method comprises pre-denaturalizing at 95° C. for 3 min; denaturalizing at 95° C. for 15 s, annealing at 60° C. for 15 s, extending at 72° C. for 60 s, repeating denaturalizing, annealing and extending for 35 times; and then extending at 72° C. for 5 min.

Also, the present invention provides an overexpression vector for expressing PpHSP21 CDS, wherein the overexpression vector takes pCAMIBA1300 as a basic carrier, and inserts the gene PpHSP21 between Xbal I and BamH I restriction sites of the basic vector. The present invention does not specifically limit the construction method of the overexpression vector, and the conventional vector construction method in the field is able to be used.

The present invention also provides applications of the gene PpHSP21 or the overexpression vector in genetic improvement of black spot disease resistance in plants. Preferably, the plants are *Pyrus* spp. or *Arabidopsis thaliana*.

The present invention also provides a method of improving black spot disease resistance in plants, which comprises a step of performing overexpression on the gene PpHSP21 in a genome of plants, wherein a nucleotide sequence of the gene PpHSP21 is shown in SEQ ID NO. 1. Preferably, performing overexpression on the gene PpHSP21 comprises connecting the gene shown in SEQ ID NO. 1 with the overexpression vector pCAMIBA1300 through homologous recombination technology, and then transforming into DH5a competent cells, plating, shaking, sequencing after sending a bacterial solution to Sangon Biotech Company, Shanghai, extracting plasmids of *Escherichia coli* with correct sequencing results with AxyPrep plasmid DNA mini extraction reagent (Axygen, USA) box, transferring 35S::P1300-PpHSP21/CDS into *Agrobacterium* competent cell (GV3101), and then infect the plant.

The gene PpHSP21 with black spot disease resistance which is isolated from *Pyrus pyrifolia* and its applications are explained in detail in combination with embodiments as follows, but these embodiments are unable to be understood as limiting the protection scope of the present invention.

First Embodiment

Cloning of Full-Length cDNA of Gene PpHSP21 Isolated from *Pyrus* Spp., and Construction of Overexpression Vector and Gene Silencing Vector The heat shock protein coding gene with strong response to black spot disease is obtained through transcriptome screening of black spot disease of *Pyrus* spp., named PpHSP21, and has a gene ID (identity document) number Pbr040066.1. According to its nucleotide sequence, the full-length and non-conservative fragment homologous recombination primers of the gene are obtained through amplification and described as follows.

The full-length homologous recombination primers are:

PpHSP21-F2 (SEQ ID NO. 5):
5'-gagaacacgggggactctagaATGGCTTCAACATTGGCTTTGTC-3';

PpHSP21-R2 (SEQ ID NO. 6):
5'-gcccttgctcaccatggatccCTGAATTGCAACGTCAATAACC-3'.

Non-conservative fragment (297 bp CDS sequence) homologous recombination primers are:

PpHSP21-F3 (SEQ ID NO. 7):
5'-aaggttaccgaattactagaGACATCAAAGACGACGAACAC-3'.

PpHSP21-R3 (SEQ ID NO. 8):
5'-tgtcttcgggacatgcccgggCTGAATTGCAACGTCAATAACC-3'.

Using cDNA of *Pyrus pyrifolia* as template for amplification with high-fidelity enzyme, wherein the amplification system is 50 μL system, which comprises 1 μL of Phanta Max Super-Fidelity DNA Polymerase, 25 μL of 2×Phanta Max Buffer, 1 μL of dNTP Mix (10 mM each), 2 μL of forward primer, 2 μL of reverse primer, 1 μL of template DNA and 18 μL of ddH$_2$O. An amplification process comprises steps of pre-denaturalizing at 95° C. for 3 min; denaturalizing at 95° C. for 15 s, annealing at 60° C. for 15 s, extending at 72° C. for 60 s, repeating denaturalizing, annealing and extending for 35 times; and then extending at 72° C. for 5 min.

PCM1300 double enzyme digestion system comprises 1 μL of Xbal I/BamH I, 5 μL of 10× concentrate CutSmart buffer, 1 μg of plasmids and a certain amount of ddH$_2$O, wherein a total amount of PCM1300 double enzyme digestion system is 10 μL. pTRV2 double enzyme digestion system comprises 1 μL of Xbal I/Sam I, 5 μL of 10× concentrate CutSmart buffer, 1 μg of plasmids and a certain amount of ddH$_2$O, wherein a total amount of PCM1300 double enzyme digestion system is 10 μL.

PCM1300 recombination system comprises 1000 ng of linearization vector, 80 ng of insertion element, 24 μL of 5×CE II Buffer, 1 μL of Exnase II and a certain amount of ddH$_2$O, wherein the PCM1300 recombination system is 10 μL.

Recovering and purifying the full length and fragment of gene with AxyPrep-96 DNA gel recovery kit (Axygene, USA), respectively connecting the 678 bp CDS sequence and the 297 bp CDS sequence with the overexpression vector pCAMIBA1300 and the gene transient silencing vector pTRV2 through homologous recombination technology, and then transforming DH5a competent cells, coating the plate, shaking the bacteria, and then sending the bacterial solution to Sangon Biotech Company, China for sequencing, extracting plasmids from *Escherichia coli* with correct sequencing results with AxyPrep plasmid DNA Mini Preparation Kit (Axygen, USA), transferring 35S::P1300-PpHSP21/CDS and pTRV2-PpHSP21/CDS into *Agrobacterium* competent cells (GV3101), and storing at −80° C. for later use.

Second Embodiment

Genetic Transformation and Positive Identification of *Arabidopsis thaliana*

(I) Genetic Transformation of *Arabidopsis thaliana*
 (1) taking *Agrobacterium* strain P1300-PpHSP21/CDS, streaking on an LB (Luria-Bertani) solid medium of the corresponding antibiotics (containing 50 mg/L Kanamycin and 50 mg/L Rifampicin) and culturing at 28° C. for 2-3 days;
 (2) performing monoclonal selection, shaking culture in an LB solution at 28° C. for 16-24 h under a rotational speed of 220 rpm;
 (3) expanding culture according to 1:100, shaking culture overnight at 28° C. and obtaining a bacteria liquid;
 (4) centrifugating the bacteria liquid at room temperature for 20 min at a rotational speed of 5000 r/min, and collecting bacteria;
 (5) suspending the bacteria in a transformation medium with a same volume of the bacteria liquid (½ MS medium, 5% sucrose, 10 μL/L 6-BA and PH=5.7);
 (6) cutting siliques and opened flowers of *Arabidopsis thaliana* to be transformed (generally when it bolts 10 cm high);
 (7) adding Sillwett-77 into a medium to be transformed till a concentration reaches 0.025%;
 (8) putting the *Arabidopsis thaliana* inflorescence into the bacterial solution, vacuuming to 380 mmHg, and soaking for 10-20 min;
 (9) moisturizing with plastic wrap, and placing in the dark at 22° C. overnight;
 (10) taking out the plant, normally culturing, and collecting seeds for screening.

(II) Screening of Transgenic *Arabidopsis thaliana* PpHSP21 Positive Seedlings

Each genetically modified material was screened according to 100 seeds per treatment, and the number of resistant seedlings was counted after 7 d and 20 d. The screen process comprises steps of:
 (1) seed disinfection which comprises performing surface disinfection on *Arabidopsis thaliana* seeds T1 with 75% alcohol for 1 min, cleaning with sterilized water for 2-3 times, then performing disinfection with 10% sodium hypochlorite for 5 min, and then cleaning with sterilized water for 3-5 times;
 (2) inoculating the sterilized seeds on ½ MS solid medium (including 50 mg/L Hygromycin, 100 mg/L Timentin and 250 mg/L Carboxylation);
 (3) treating in a refrigerator at 4° C. in the dark for 2 days, then transferring to an incubator (with 16 hours light/8 hours dark, the light intensity of 8000 Lux, and temperature of 23° C.);
 (4) observing seed growth, wherein the non-transgenic seedlings turn yellow and gradually die, while transgenic plants will grow; and
 (5) when the green seedlings grow to 4 cotyledons, transferring to nutrient soil for cultivation.

Repeating the above steps for continuous screening, T3-generation PpHSP21 and transgenic *Arabidopsis thaliana* for functional verification.

(III) Molecular Detection of Transgenic *Arabidopsis thaliana*

The method of DNA extraction from transgenic *Arabidopsis thaliana* leaves comprises steps of:
 (1) putting a small amount of *Arabidopsis thaliana* leaves into a 1.5 mL centrifuge tube, grinding to powder with liquid nitrogen, adding 600 μL of CATB extract, wherein the preparation method of CTAB extract is shown in Table 1;
 (2) after mixing thoroughly, performing bath in a 65° C. water bath for 90 min, wherein the liquid is mixed upside down every 30 min during this period;
 (3) after the water bath is completed, adding 700 μL of 24:1 (chloroform:isoamyl alcohol) mixed extract, vigorously inverting and mixing, centrifuging at 12000 r/min for 15 min at room temperature, and transferring the supernatant (about 500 μL) to a new 1.52 mL centrifuge tube;

4) adding the same volume of pre-cooled isopropanol as the supernatant, mixing upside down and placing in a refrigerator at −20° C. for precipitation, wherein the precipitation time is able be extended;

(5) after the precipitation is completed, taking out and centrifuging at 12000 r/min for 10 min, removing the supernatant, adding 1 mL of pre-cooled 75% ethanol, washing for 3-5 times, removing the alcohol, and air drying in a fume hood; and 6) adding 20-30 μL of ddH$_2$O to each tube to dissolve the DNA, and storing the dissolved DNA in a refrigerator at −20° C.

For concentration detection, taking 1 μL of each sample and measuring with NanoDrop2000 ultra-micro spectrophotometer (Thermo, USA). When the ratio of OD260/OD280 is in the range of 1.8-2.0, DNA purity is high. It is also detected by gel electrophoresis.

TABLE 1

CTAB extract formula

| Reagent | Volume/Weight |
|---|---|
| 1 mol/L Tris-HCl | 10 mL |
| 0.5 mol/L EDTA | 4 mL |
| 5 mol/L NaCl | 28 mL |
| CTAB | 2 g |
| PVP | 2 g |
| ddH$_2$O | supplemented for 98 mL water bath at 65° C. for sufficiently dissolving |
| β-mercaptoethanol (added before using) | 2 mL |

The above-mentioned extracted DNA was taken as a template and PCR identification with gene-specific primers is performed to obtain multiple positive plants, as shown in FIG. 7A. The primer sequences are PpHSP21-F1 (SEQ ID NO. 3): ATGGCTTCAACATTGGCTTTGTC, PpHSP21-R1 (SEQ ID NO. 4): CTGAATTGCAACGTCAATAACC. In addition, the PpHSP21 gene of the obtained positive plants was analyzed semi-quantitatively, and *Arabidopsis thaliana* AtActin was taken as an internal reference. Primer sequences of the internal reference were AtActin-F (SEQ ID NO. 9): 5'-GGTGTCATGGTTGGTATGGGTC-3' and AtActin-R (SEQ ID NO. 10): 5'-CCTCTGTGAGTAGAACTGGGTGC-3', semi-quantitative primer sequences are PpHSP21-F4 (SEQ ID NO. 11): 5'-TCTCCTTTTGGTATTGCAGGTCT-3' and PpHSP21-R4 (SEQ ID NO. 12): 5'-GGCATGTCGAACCGCATTTT-3'. The results showed that the positive lines #5, #6, and #14 had higher expression levels of PpHSP21 (FIGS. 7B and 7C) under the condition of consistent brightness of the internal control, which was selected for subsequent experimental function verification.

Third Embodiment

Figure 3A:
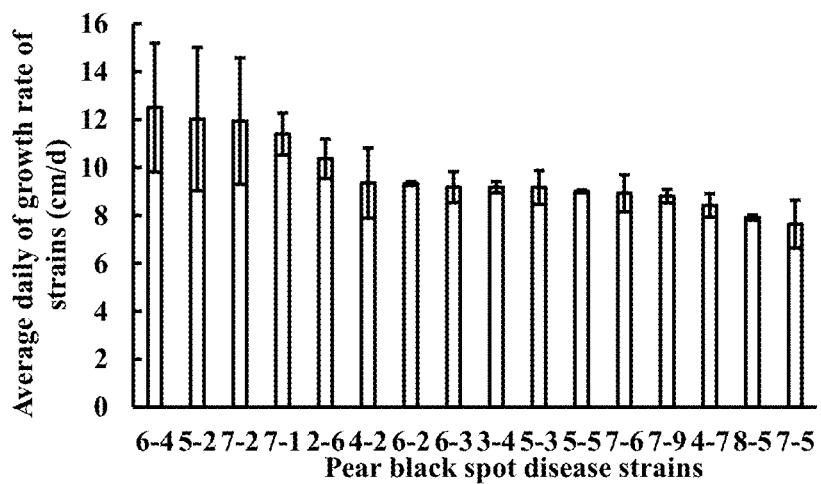
FIG. 3A shows the average daily growth rate of different black spot disease strains.
Figure 3B:
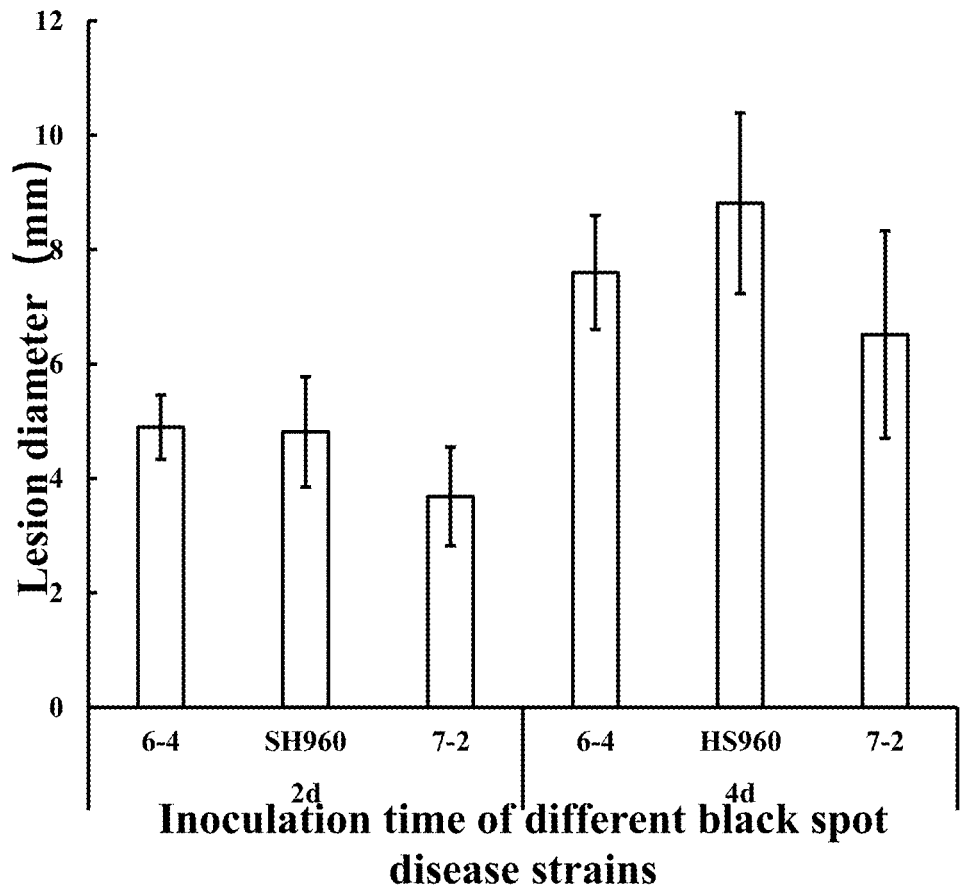
FIG. 3B shows the difference in pathogenicity of three black spot disease strains.
Figure 3C:
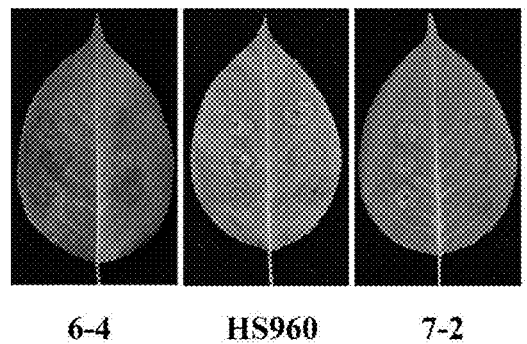
FIG. 3C shows the phenotype of three black spot disease strains after 4 days of being inoculated with leaves of 587 cultivar, respectively.
Figure 4:
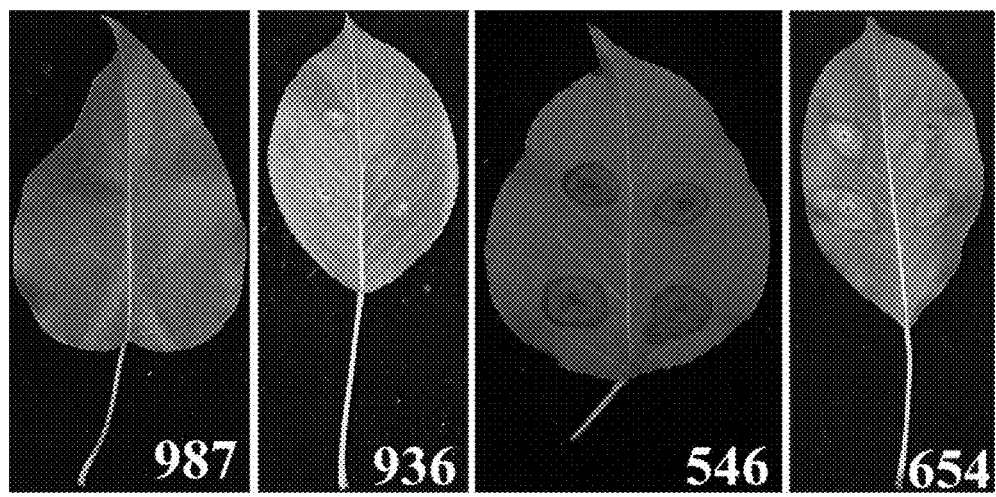
FIG. 4 shows some highly resistant and highly susceptible cultivars among 190 *Pyrus* spp. cultivars from Hushu, China, wherein 987 and 936 are highly resistant cultivars, 546 and 654 are highly susceptible cultivars.
Figure 5:
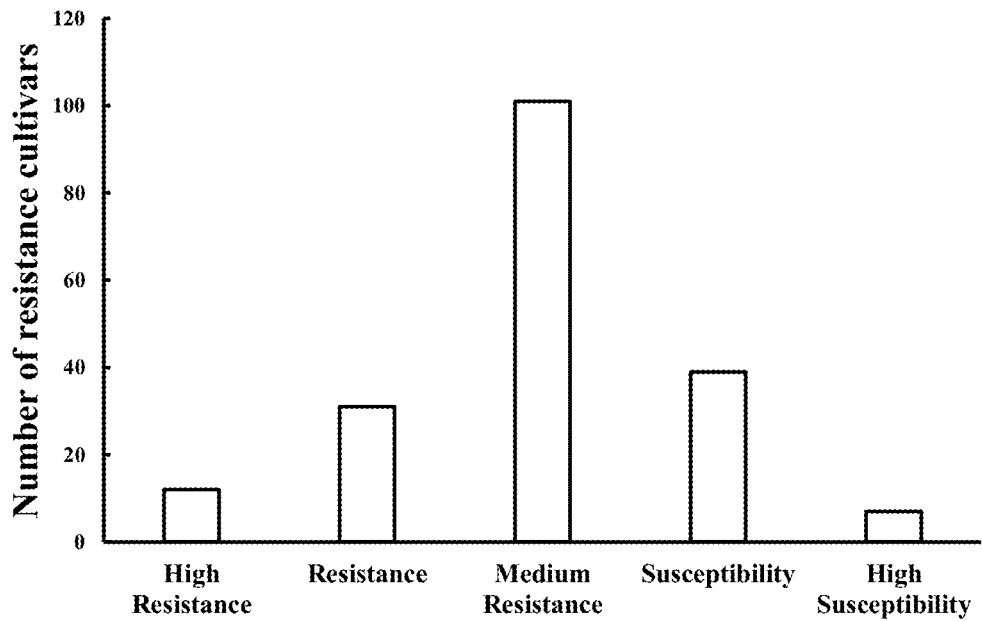
FIG. 5 shows the evaluation to black spot disease resistance of 190 *Pyrus* spp. cultivars from Hushu, China.

Field Evaluation of 190 *Pyrus* Spp. Cultivars Inoculated with Black Spot Disease From 40 black spot disease strains, which are 38 black spot disease strains collected by the Jiangsu Academy of Agricultural Sciences, China, 1 black spot disease strain collected by Anhui Agricultural University, China and 1 black spot disease strain collected by Hushu base, China, 16 black spot disease strains with obvious differences in shape and color were selected as experimental strains. The 16 black spot disease strains were respectively placed in a PDA culture medium for activation and were cultured for 4 days in a 28° C. light incubator, multiple holes were punched at edges of strains with a hole puncher, the strains were placed into a new culture medium, every treatment is repeated for twice, the strains were cultured for 4 days in the 28° C. light incubator, an average growth rate of black spot disease was calculated; referring to FIG. 3A, the black spot disease strains 6-4 and 7-2 with strong pathogenicity were screened out for later inoculation experiments. There were 3-6 disease-free leaves were picked from the top of the new shoot of the Hushu pear cultivar 587 (pear cultivar number). The leaves were sterilized with 0.2% NaClO for 30 S and washed with sterile water for 5 times, and then the leaves were placed on a porcelain dish with sterilized and moistened gauze, and then four holes were punched in the leaves with a sterile needle, and then the leaves were wetted with plastic wrap and recovered for 12 h. Holes are punched at edges of black spot disease strains 6-4 and 7-2 which had been cultured for 4 days, and then the strains were inoculated on the recovered leaves, and then the leaves were cultured in the culture box at 28° C. for 4 days, bacterial cakes were removed after two days, the diameter of disease spots on the leaves after 2 days and 4 days of different strains being inoculated with the 587 cultivar was respectively counted, referring to FIG. 3B. Finally, the black spot disease strains 6-4 and HS960 with strong pathogenicity were selected for late inoculation experiments, referring to FIG. 3C. According to the leaf disease resistance grade classification standard of Jiangsu Province, China, and the standard was slightly modified, a new leaf disease grade classification standard was formulated, referring to Table 2. The black spot disease index was calculated according to the damage level, the disease index=100×Σ(number of diseased leaves in each disease level×corresponding disease level)/(total number of leaves×highest disease level). According to the disease index and disease resistance grade classification standard (Table 3), 190 *Pyrus* spp. cultivars from Hushu were evaluated on black spot disease resistance, and 12 high-resistant cultivars, 31 disease-resistant cultivars, 101 medium-resistant cultivars, 39 susceptible cultivars and 7 highly susceptible cultivars were identified, referring to FIG. 5.

TABLE 2

Leaf Disease Grade Classification Standard

| Disease Level | Grading Standard |
|---|---|
| 0 | The disease spot was not spread |
| 1 | 0 mm < disease spot diameter ≤ 8 mm |
| 3 | 8 mm < disease spot diameter ≤ 12 mm |
| 5 | 12 mm < disease spot diameter ≤ 16 mm |
| 7 | 16 mm < disease spot diameter ≤ 20 mm |
| 9 | 20 mm < disease spot diameter |

TABLE 3

Leaf Disease Resistance Grade Classification Standard

| Disease Resistance Level | Grading Standard |
|---|---|
| High Resistance | Disease Index ≤ 15 |
| Resistance | 15 < Disease Index ≤ 25 |
| Medium Resistance | 25 < Disease Index ≤ 40 |

TABLE 3-continued

Leaf Disease Resistance Grade Classification Standard

| Disease Resistance Level | Grading Standard |
|---|---|
| Medium Susceptibility | 40 < Disease Index ≤ 55 |
| High Susceptibility | 55 < Disease Index ≤ 100 |

Figure 6A:
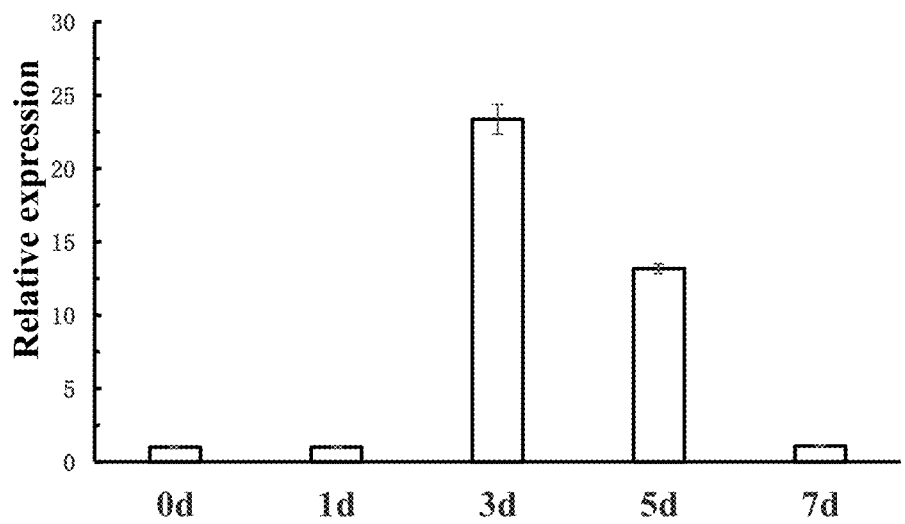
FIG. 6A shows the relative expression of PpHSP21 under black spot stress.

In order to further analyze the response mode of the gene PpHSP21 to the black spot disease, according to the present invention, leaves of Qiuzi pears were inoculated with black spot disease strains, and samples were respectively taken before treatment and were treated for 0.5 d, 3 d, 5 d and 7 d, respectively. The Tubulin of pears was taken as an internal reference, the primer sequences are Tublin-F (SEQ ID NO. 13): 5'-TGGGCTTTGCTCCTCTTAC-3'; Tublin-R: 5'-CCTTCGTGCTCATCTTACC (SEQ ID NO. 14)-3', the primer sequences of gene were PpHSP21-F4 (SEQ ID NO. 11)-TCTCCTTTTGGTATTGCAGGTCT-3'; PpHSP21-R4 (SEQ ID NO. 12): 5'-GGCATGTCGAACCGCATTTT-3'. The relative expression level was analyzed. As shown in FIG. 6A, it was able to be seen that the response of PpHSP21 gene to black spot disease was strong at 3 d after treatment, and the expression level thereof was decreased with the extension of treatment time. The seedlings of the medium-resistant cultivar 'Dangshansuli' pears were inoculated with black spot disease strains, and the sampling time was 0 d, 2 d, 4 d, 6 d and 10 d. The relative expression level was also analyzed. As shown in FIG. 6B, it was able to be seen that the response of PpHSP21 gene to black spot disease was strong at 4 d after treatment. The RNA extraction was performed with the fortune plant total RNA extraction kit. The synthesis of the first strand of the cDNA referred to the operation manual of the TransGen reverse transcription kit (TransGen Biotech, China). The quantitative PCR reaction process comprises pre-denaturalizing at 95° C. for 3 min; denaturalizing at 95° C. for 3 s, annealing at 60° C. for 10 s, extending at 72° C. for 30 s, repeating denaturalizing, annealing and extending for 45 times; and then extending at 95° C. for 5 s and at 65° C. for 1 min.

Fourth Embodiment

Analysis of Black Spot Disease Resistance in Transgenic PpHSP21 *Arabidopsis thaliana*

Figure 8A:
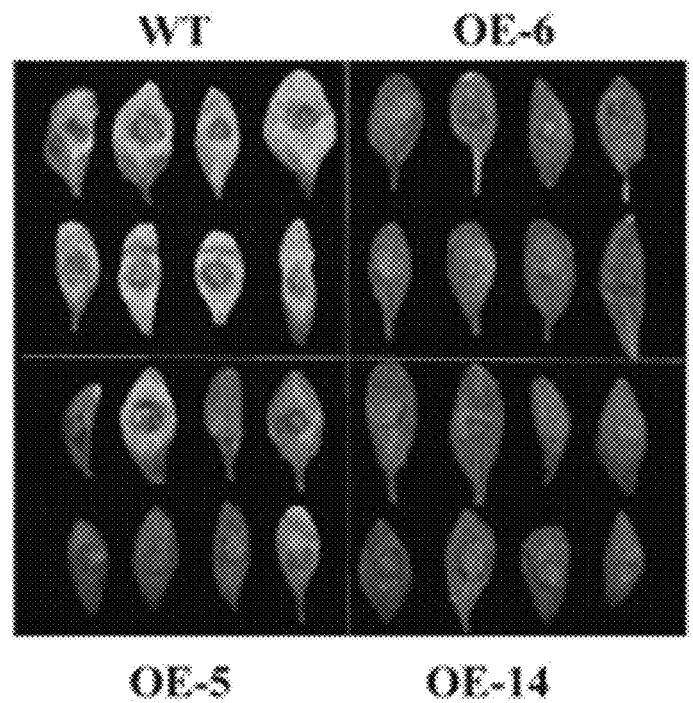
FIG. 8A shows the phenotype of 21-day-old *Arabidopsis thaliana* leaves after 4 days of treatment on black spot disease.
Figure 8B:
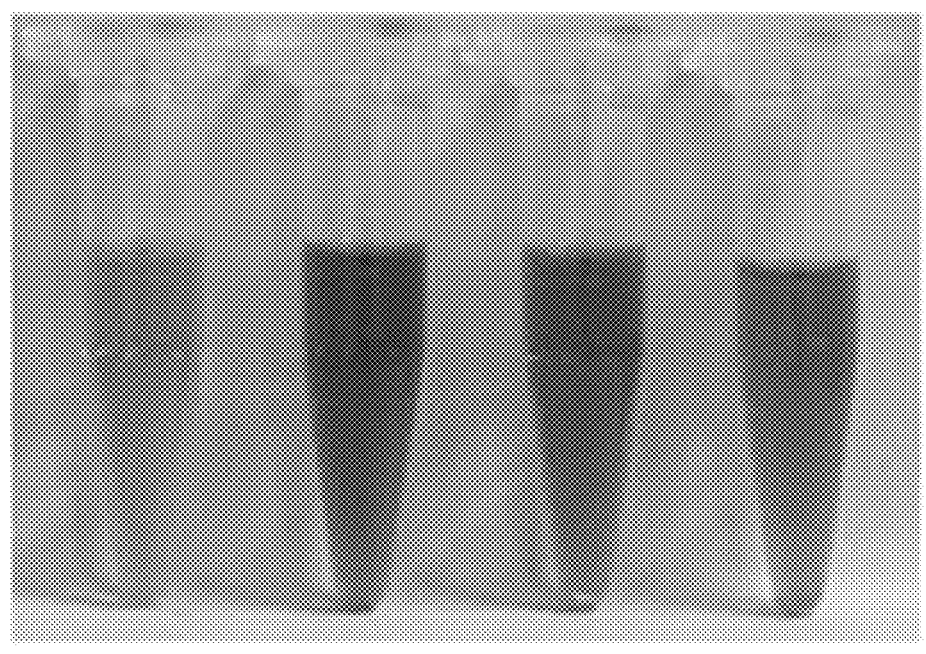
FIGS. 8B and 8C are chlorophyll extraction and chlorophyll determination of 21-day-old *Arabidopsis thaliana* leaves after 4 days of treatment on black spot disease, respectively.
Figure 8C:
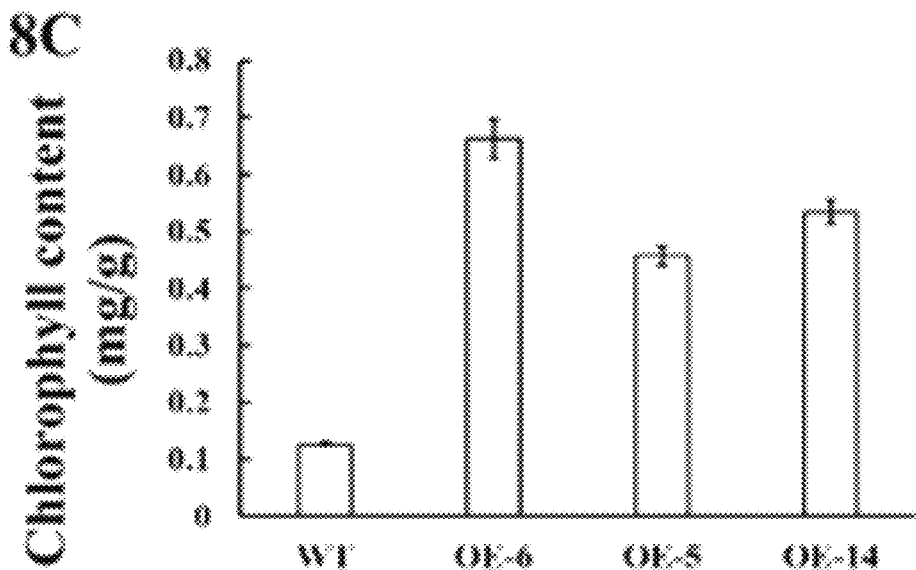

In order to further verify the black spot disease resistance in transgenic P1300-PpHSP21/CDS *Arabidopsis thaliana*, the wild-type *Arabidopsis thaliana* (hereinafter referred to as WT) and overexpression lines 5, 6, 14 (hereinafter referred to as OE-5, OE-6 and OE-14) were cultivated in nutrient soil. Eight leaves with the same physiological state were selected from each plant, and then were inoculated with black spot disease strains by the detached leaf method, and then the phenotype was observed after 48 h. As shown in FIG. 8A, it is able to seen that compared with WT, OE-5, OE-6 and OE-14 have a milder incidence of black spot disease after inoculation, indicating that PpHSP21 is able to enhance the black spot disease resistance in plants. By measuring the chlorophyll of plant leaves, the stress resistance of plants was able to be evaluated. When plants were subjected to external stress, this parameter was significantly reduced. Therefore, after 4 days of treatment on black spot disease, the chlorophyll analysis of WT, OE-5, OE-6 and OE-14 showed that the chlorophyll content of OE-5, OE-6 and OE-14 was significantly higher than that of WT, as shown in FIGS. 8B and 8C, indicating that PpHSP21 enhances the black spot disease resistance in plants.

Figure 9A:
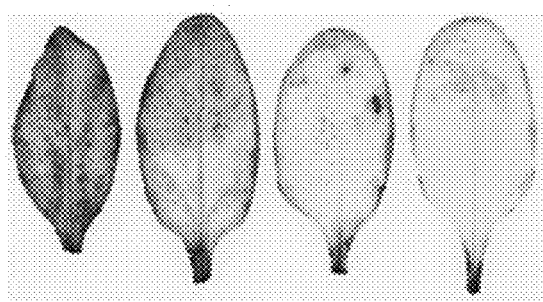
FIG. 9A shows the DAB staining of wild-type and transgenic lines after 4 days of treatment on black spot disease.
Figure 9B:
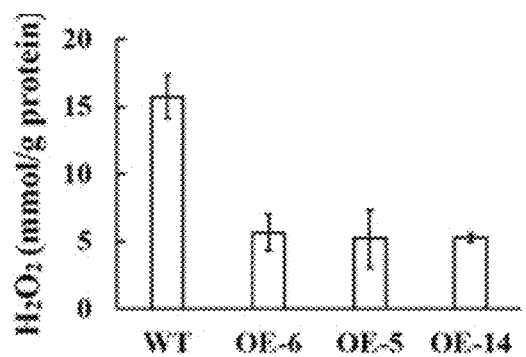
FIG. 9B shows the $H_2O_2$ content measurement of wild-type and transgenic lines after 4 days of treatment on black spot disease.

The wild-type *Arabidopsis thaliana* and transgenic *Arabidopsis thaliana* were performed histochemical staining with diaminobenzidine (DAB), and $H_2O_2$ accumulation was qualitatively analyzed. Results showed that after 4 days of treatment on black spot disease, the $H_2O_2$ content of OE-5, OE-6, OE-14 was significantly lower than that of WT, as shown in FIG. 9A. After 4 days of treatment on black spot disease, the $H_2O_2$ content of wild-type *Arabidopsis thaliana* and transgenic *Arabidopsis thaliana* (hydrogen peroxide extraction kit, prepared in Nanjing, China) was measured. The $H_2O_2$ content of wild-type *Arabidopsis thaliana* was higher than that of transgenic *Arabidopsis thaliana*, as shown in FIG. 9B, which showed that PpHSP21 participated in the removal of reactive oxygen species and enhanced the plant tolerance to stress. In summary, PpHSP21 has the function of enhancing the black spot disease resistance in plants.

Fifth Embodiment

VIG S Material Identification and Analysis of Black Spot Disease Resistance (1) *Pyrus betulifolia* was Transformed with the Instant Method The pTRV1 *Agrobacterium* and pTRV2 *Agrobacterium* were cultivated, respectively, pTRV1 plaques and pTRV2 plaques after the second marking were collected, the OD value of two liquids was adjusted to 1.0 with an infection solution whose formula is shown in Table 4, and then leaves of 60-day *Pyrus betulaefolia* were injected with 100 mM/L of Acetosyringone (AS) which is added with a mixture of pTRV1 *Agrobacterium* and pTRV2 *Agrobacterium* with a ratio of 1:1, so as to silence PpHSP21 gene in *Pyrus betulaefolia*. *Pyrus betulaefolia* is protected from light for 2 to 3 days at room temperature and maintains a certain humidity after injection.

TABLE 4

Formula of infection solution

| Drug Name | Concentration and pH |
|---|---|
| MES mother liquid | 200 mM (the solvent is distilled water) and pH is adjusted to 5.7 with KOH |
| $MgCl_2$ mother liquid | 200 mM, the solvent is distilled water |
| Infection Solution | 100 mL of infection solution including 5 mL of MES mother liquid, 5 mL of $MgCl_2$ mother liquid and 90 mL of distilled water |

(2) Molecular Detection of Gene Silencing *Pyrus betulifolia* Lines

The DNA extraction method of the present embodiment is the same as that of the second embodiment.

(3) RNA Extraction and Semi-Quantitative Analysis

The silencing effect of *Pyrus betulifolia* lines with PpHSP21 gene silencing was analyzed, and Tubulin of *Pyrus betulifolia* lines was taken as an internal reference, primer sequences of the internal reference are Tubulin-F (SEQ ID NO. 13): 5'-TGGGCTTTGCTCCTCTTAC-3' and Tubulin-R (SEQ ID NO. 14): 5'-CCTTCGTGCTCATCT-TACC-3'; semiquantitative primer sequences are PpHSP21-F4 (SEQ ID NO. 11): 5'-TCTCCTTTTGGTATTGC-AGGTCT-3'; PpHSP21-R4 (SEQ ID NO. 12): 5'-GG-CATGTCGAACCGCATTTT-3'. Results showed that in the case of the same brightness of the internal reference shown in FIG. 7D, gene silencing lines #1, #2, and #3 (hereinafter referred to as TRV2-1, TRV2-2 and TRV2-3)

have the best silencing effect of PpHSP21 shown in FIG. 7E, so that TRV2-1, TRV2-2 and TRV2-3 are selected for subsequent experimental function verification.

Figure 8D:
FIG. 8D shows the phenotype of 60-day-old *Pyrus betulifolia* leaves after 5 days of treatment on black spot disease.
Figure 8E:
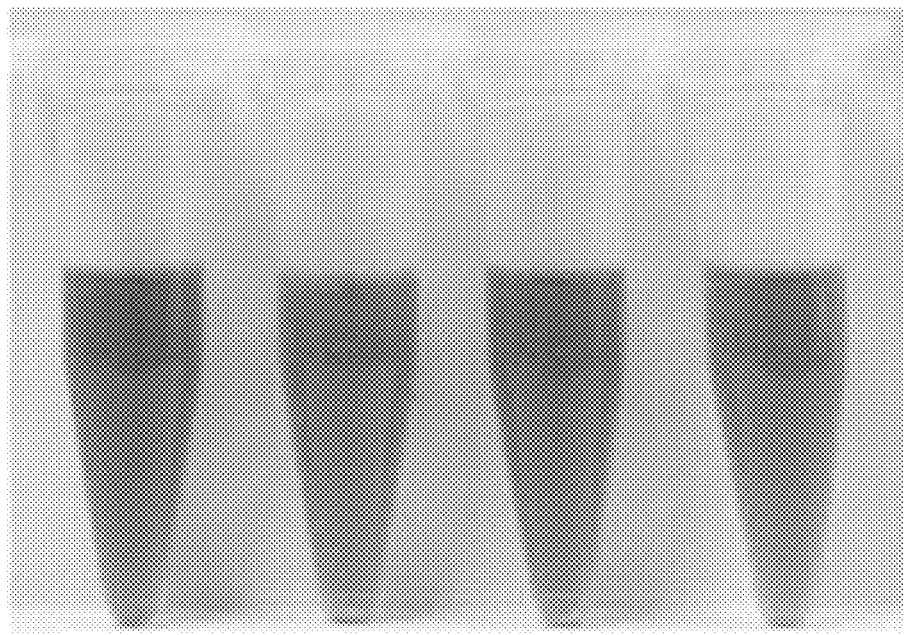
FIGS. 8E and 8F are chlorophyll extraction and chlorophyll determination of 60-day-old *Pyrus betulifolia* leaves after 5 days of treatment on black spot disease, respectively.
Figure 8F:
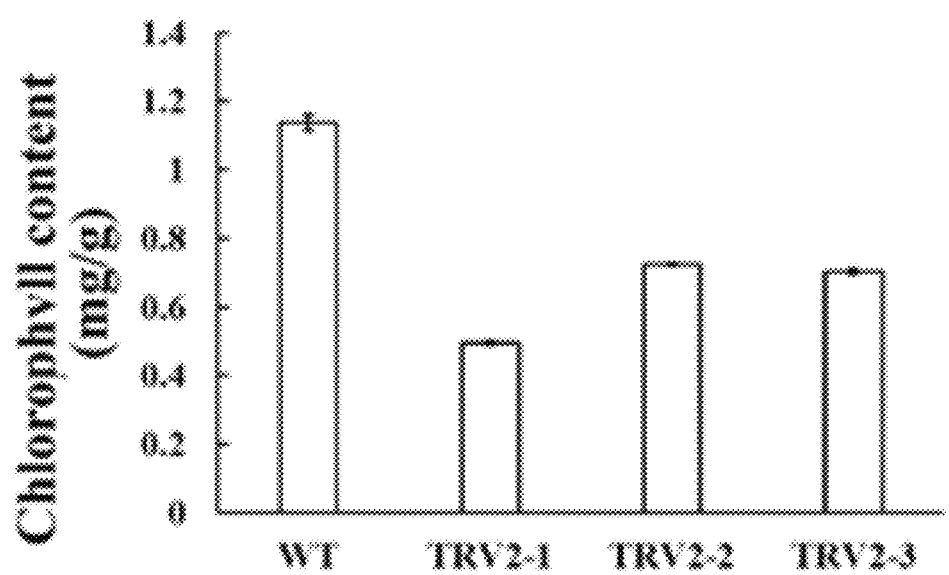
Figure 9C:
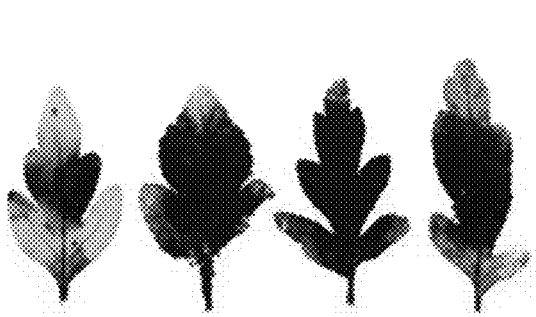
FIG. 9C shows the DAB staining of wild-type and gene-silenced *Pyrus betulaefolia* lines after 5 days of treatment on black spot disease.
Figure 9D:
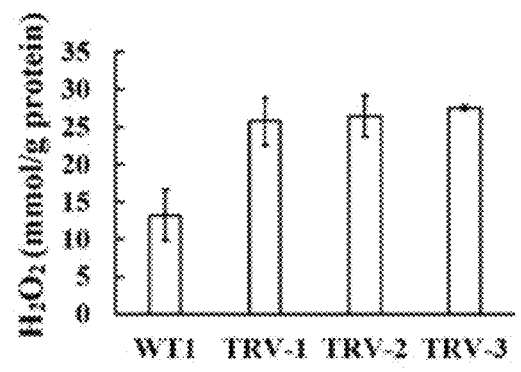
FIG. 9D shows the $H_2O_2$ content measurement of wild-type and gene-silenced *Pyrus betulaefolia* lines after 5 days of treatment on black spot disease.

In order to further verify the black spot disease resistance of TRV2-1, TRV2-2 and TRV2-3, *Pyrus betulifolia* (WT, TRV2-1, TRV2-2, TRV2-3) were cultivated in nutrient soil. Six leaves with the same physiological state were selected from each plant, and then were inoculated with pathogenic black spot disease strain 6-4 by the detached leaf method, and then the phenotype was observed after 5 days. As shown in FIG. 8D, it is able to seen that compared with WT, PpHSP21 gene silencing lines TRV2-1, TRV2-2 and TRV2-3 have severe disease after inoculation with black spot disease lines shown in FIG. 8D, indicating that PpHSP21 is able to enhance the black spot disease resistance in plants. By measuring the chlorophyll of plant leaves, the stress resistance of plants was able to be evaluated. When plants were subjected to external stress, this parameter was significantly reduced. Therefore, after 5 days of treatment on black spot disease, the chlorophyll analysis of WT, TRV2-1, TRV2-2 and TRV2-3 showed that the chlorophyll content of gene silencing lines TRV2-1, TRV2-2 and TRV2-3 was significantly lower than that of WT, as shown in FIGS. 8E and 8F, indicating that silencing PpHSP21 gene reduces the black spot disease resistance in plants. After 5 days of treatment on black spot disease, the *Pyrus betulifolia* leaves were performed histochemical staining with diaminobenzidine (DAB), and $H_2O_2$ accumulation was qualitatively analyzed. Results showed that after treatment on black spot disease, the $H_2O_2$ content of TRV2-1, TRV2-2 and TRV2-3 was significantly higher than that of WT, as shown in FIG. 9C. At the same time, the $H_2O_2$ content of WT, TRV2-1, TRV2-2 and TRV2-3 (hydrogen peroxide extraction kit, prepared in Nanjing, China) was measured. The $H_2O_2$ content of WT was lower than that of TRV2-1, TRV2-2 and TRV2-3, as shown in FIG. 9D, which showed that PpHSP21 reduces the plant tolerance to stress of black spot disease.

The above are only the preferred embodiments of the present invention. It should be pointed out that for those skilled in the art, under the premise of not departing from the principle of the present invention, several improvements and modifications are able to be made, and these improvements and modifications should also be regarded as the protection scope of the present invention.

What is claimed is:

1. A method of improving a plant's, or plant cell's, resistance to black spot disease caused by *Alternaria alternata*, comprising:

(a) introducing into the genome of a plant, or a plant cell, a polynucleotide molecule comprising the nucleic acid sequence SEQ ID NO: 1, (b) overexpressing the nucleic acid sequence within the plant or plant cell, and (c) selecting a plant or plant cell from (b) for having improved resistance to blackspot disease caused by *Alternaria alternata* as compared to that of a plant, or a plant cell, within which the nucleic acid sequence is not overexpressed.

* * * * *